(12) United States Patent
Kirsch et al.

(10) Patent No.: US 7,041,345 B2
(45) Date of Patent: May 9, 2006

(54) CHIRAL COMPOUNDS III

(75) Inventors: Peer Kirsch, Darmstadt (DE); Andreas Tangerbeck, Darmstadt (DE); Detlef Pauluth, Ober-Ramstadt (DE); Joachim Krause, Dieburg (DE); Michael Heckmeier, Bensheim (DE); Kazuaki Tarumi, Seeheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/332,807

(22) PCT Filed: Jun. 25, 2001

(86) PCT No.: PCT/EP01/07218

§ 371 (c)(1),
(2), (4) Date: Jan. 13, 2003

(87) PCT Pub. No.: WO02/00265

PCT Pub. Date: Jan. 24, 2002

(65) Prior Publication Data

US 2003/0189189 A1  Oct. 9, 2003

(30) Foreign Application Priority Data

Jul. 13, 2000 (EP) ................... 00115249

(51) Int. Cl.
*C09K 19/52* (2006.01)
*C09K 19/38* (2006.01)
*C09K 19/36* (2006.01)
*C07D 317/10* (2006.01)
*C07D 317/20* (2006.01)

(52) U.S. Cl. ............... 428/1.1; 252/299.01; 252/299.7; 549/430; 549/451; 549/453; 549/455

(58) Field of Classification Search ............... 428/1.1; 252/299.5, 299.01; 549/430, 451, 453, 455
See application file for complete search history.

(56) References Cited

U.S. PATENT DOCUMENTS

| | | | | |
|---|---|---|---|---|
| 5,112,689 A | * | 5/1992 | Ueno et al. ............. | 428/407 |
| 6,099,751 A | * | 8/2000 | Meyer et al. ........... | 252/299.61 |
| 6,183,822 B1 | * | 2/2001 | Farrand et al. ......... | 428/1.1 |
| 6,607,677 B1 | * | 8/2003 | Buchecker et al. .... | 252/299.01 |
| 6,830,789 B1 | * | 12/2004 | Doane et al. ........... | 428/1.3 |
| 2002/0187281 A1 | * | 12/2002 | Doane et al. ........... | 428/1.1 |

FOREIGN PATENT DOCUMENTS

| DE | 19611101 A | 9/1997 |
|---|---|---|
| WO | 9964383 A | 12/1999 |

OTHER PUBLICATIONS

Kuball et al., "TADDOLs with Unprecedented Helical Twisting Power in Liquid Crystals", Helvetical Chimica Acta., 1997, vol. 80, pp. 2507-2514.*
Caplus 1999: 735300.*
Kuball, H-G., "TADDOLS with unprecedented helical twisting power in liquid crystals," Helvetica Chimica ACTA, Verlag Helvetica Chimica ACTA, Basel, Ch, vol. 8, No. 80, pp. 2507-2514, XP002076376, ISSN: 0018-019X.
Kuball, H-G., "Chirality and Circular dichorism of oriented molecules and anisotropic phases," Chirality (2000), 12(4), 278-286, XP001041318.
Seebach, D. et al., "Preparation of TADDOL Derivatives for New Applications," Org. Lett. (1999), 1(1), 55-58, XP001041200.

\* cited by examiner

*Primary Examiner*—Shean C. Wu
(74) *Attorney, Agent, or Firm*—Millen, White, Zelano, Branigan, P.C.

(57) ABSTRACT

The invention relates to chiral compounds of formula (I) wherein $Y^1$, $Y^2$, $Y^3$, $Y^4$, $X^1$, $X^2$, $X^3$ and $X^4$ have the meaning given in claim 1, to liquid crystalline mixtures comprising at least one chiral compound of formula (I), to chiral linear or crosslinked liquid crystalline polymers obtainable by polymerizing a polymerizable mixture comprising at least one chiral compound of formula (I), to the use of chiral compounds of formula (I) and mixtures and polymers obtained thereof in liquid crystal displays, active and passive optical elements, adhesives, synthetic resins with anisotropic mechanical properties, cosmetic and pharmaceutical compositions, diagnostics, liquid crystal pigments, for decorative and security applications, nonlinear optics, optical information storage or as chiral dopants, and to a liquid crystal display comprising a mixture comprising at least one chiral compound of formula (I)

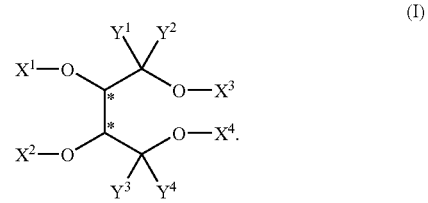

21 Claims, No Drawings

CHIRAL COMPOUNDS III

The invention relates to chiral compounds, to liquid crystalline mixtures containing the chiral compounds, to polymers obtained from the chiral compounds and liquid crystalline mixtures, and to the use of the chiral compounds, liquid crystalline mixtures and polymers obtained thereof in liquid crystal displays, active and passive optical elements like polarizers, compensators, alignment layers, colour filters or holographic elements, in adhesives, synthetic resins with anisotropic mechanical properties, cosmetic and pharmaceutical compositions, diagnostics, liquid crystal pigments, for decorative and security applications, in nonlinear optics, optical information storage or as chiral dopants.

Chiral compounds can be used as dopants to induce or enhance a helical twist in a liquid crystalline mixture that is used for example in liquid crystal displays. The pitch p of the molecular helix in the first approximation, which is sufficient for most practical applications, is inversely proportional to the concentration c of the chiral dopant in the liquid crystal host mixture according to equation (1):

$$p = \frac{1}{HTP} \cdot \frac{1}{c} \quad (1)$$

The proportionality factor is the helical twisting power (HTP) of the chiral dopant.

For many applications it is desirable to have LC mixtures with a twisted phase. Among these are e.g. phase-change displays, guest-host displays, passive and active matrix TN and STN displays like AMD-TN, ferroelectric displays and cholesteric displays like SSCT (surface stabilized cholesteric texture) or PSCT (polymer stabilized cholesteric texture) displays, including displays with temperature compensated characteristics, e.g. by appropriate selection of the cholesteric compounds according to the invention either alone or in combination with further chiral dopants. For these applications it is advantageous to have available a chiral dopant with a high HTP in order to reduce the amount of dopant needed to induce the desired pitch.

For some applications it is desired to have LC mixtures that exhibit a strong helical twist and thereby a short pitch length. For example in liquid crystalline mixtures that are used in selectively reflecting cholesteric displays like SSCT or PSCT, the pitch has to be selected such that the maximum of the wavelength reflected by the cholesteric helix is in the range of visible light. Another possible application are polymer films with a chiral liquid crystalline phase for optical elements, such as cholesteric broadband polarizers or chiral liquid crystalline retardation films.

As can be seen from equation (1), a short pitch can be achieved by using high amounts of dopant or by using a dopant with a high HTP.

D. Seebach et al., *Chimia* 1991, 45, 238–244 and H.-G. Kuball et al., *Helv. Chim. Acta* 1997, 80, 2507–2514 reported that derivatives of α,α, α',α'-tetraaryl-1,3-dioxolan-4,5-dimethanol (TADDOL) show high HTP values. WO 97/34886 discloses polymerizable TADDOL derivatives.

However, when using chiral dopants of prior art in high amounts, they often negatively affect the properties of the liquid crystalline host mixture, such as e.g. the clearing point, the dielectric anisotropy $\Delta\epsilon$, the viscosity, the driving voltage or the switching times. Also, polymerizable compounds tend to show spontaneous polymerization and are not suitable for display applications where only low molar mass mixtures are used.

Another disadvantage of prior art chiral compounds is that they often show low solubility in the liquid crystal host mixture, which leads to undesired crystallization at low temperatures. To overcome this disadvantage, typically two or more different chiral dopants have to be added to the host mixture. This implies higher costs and also requires additional effort for temperature compensation of the mixture, as the different dopants have to be selected such that their temperature coefficients of the twist compensate each other.

Consequently, there is a considerable demand for chiral compounds with a high HTP which are easy to synthesize, can be used in low amounts, show improved temperature stability of the cholesteric pitch e.g. for utilizing a constant reflection wavelength, do not affect the properties of the liquid crystalline host mixture and show good solubility in the host mixture.

The invention has the aim of providing chiral compounds having these properties, but which do not have the disadvantages of the chiral dopants of the state of the art as discussed above.

Another aim of the invention is to extend the pool of chiral compounds that can be used as dopants available to the expert.

It has been found that these aims can be achieved by providing chiral compounds of formula I.

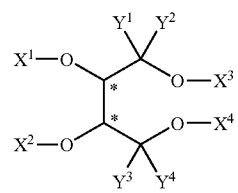

I wherein
$X^1$ and $X^2$ are H or form together a bivalent radical selected from —$CH_2$—, —$CHR^1$—, —$CR^1R^2$—, —$SiR^1R^2$— or 1,1-cycloalkyliden,
$X^3$ and $X^4$ have one of the meanings given for $X^1$ and $X^2$,
$Y^1$, $Y^2$, $Y^3$ and $Y^4$ are each independently $R^1$, A or M-$R^3$,
A is a cyclic group,
M is a mesogenic group,
$R^1$ and $R^2$ have independently from each other one of the meanings of $R^3$ or denote -M-$R^3$,
$R^3$ is H, F, Cl, Br, CN, SCN, $SF_5$, or a chiral or achiral alkyl group with up to 30 C atoms which may be unsubstituted, mono- or polysubstituted by F, Cl, Br or CN, it being also possible for one or more non-adjacent $CH_2$ groups to be replaced, in each case independently from one another, by —O—, —S—, —NH—, —N($CH_3$)—, —CO—, —COO—, —OCO—, —OCO—O—, —S—CO—, —CO—S—, —CH=CH— or —C≡C— in such a manner that oxygen atoms are not linked directly to one another, or a polymerizable group, wherein at least one of $Y^1$, $Y^2$, $Y^3$ and $Y^4$ is M-$R^3$.

Another object of the invention is a liquid crystalline mixture containing at least one compound of formula I.

Another object of the present invention is a polymerizable liquid crystalline mixture comprising at least one compound of formula I and at least one polymerizable mesogenic compound having at least one polymerizable functional group.

Another object of the invention is a chiral linear or crosslinked liquid crystalline polymer obtainable by polymerizing a polymerizable liquid crystalline mixture comprising one or more compounds of formula I.

A further object of the invention is the use of a chiral compound, mixture or polymer as described above in liquid crystal displays, such as STN, TN, AMD-TN, temperature compensation, ferroelectric, guest-host, phase change or surface stabilized or polymer stabilized cholesteric texture (SSCT, PSCT) displays, in active and passive optical elements like polarizers, compensators, alignment layers, colour filters or holographic elements, in adhesives, synthetic resins with anisotropic mechanical properties, cosmetic and pharmaceutical compositions, diagnostics, liquid crystal pigments, for decorative and security applications, in nonlinear optics, optical information storage or as chiral dopants.

Yet another object of the invention is a liquid crystal display comprising a liquid crystalline mixture or a polymerizable liquid crystalline mixture comprising at least one chiral compound of formula I.

The inventive chiral compounds bear several advantages
- they exhibit a good solubility in liquid crystalline mixtures,
- they exhibit broad liquid crystalline phases,
- when inventive compounds are used as chiral dopant in a liquid crystalline mixture, due to their high solubility higher amounts of dopant can be used to produce a high twist (=a low pitch),
- in case high amounts of dopants are needed, due to the broad liquid crystalline phases of the inventive dopants the liquid crystal phase of the host mixture is less negatively influenced,
- in case of inventive compounds with high HTP, lower amounts are needed to achieve a high pitch, and thereby the liquid crystalline properties of the mixture are less negatively affected,
- enantiomerically pure chiral compounds are easy to prepare from cheap, readily available starting materials,
- the availability of both helices is a considerable advantage, e.g. for the use in security applications, as it enables the production of chiral films or coatings reflecting circularly polarized light of a single handedness.

The chiral compounds of the present invention are mesogenic or even liquid crystalline, i.e. they can induce or enhance mesophase behaviour for example in admixture with other compounds, or even exhibit one or more mesophases themselves. It is also possible that the inventive compounds show mesophase behaviour only in mixtures with other compounds, or, in case of polymerizable compounds, when being (co)polymerized. Mesogenic chiral compounds are especially preferred.

The groups $Y^1$, $Y^2$, $Y^3$ and $Y^4$ in formula I can be identical or different. Especially preferred are compounds wherein $Y^1$, $Y^2$, $Y^3$ and $Y^4$ are identical. Further preferred are compounds with two different pairs of groups $Y^1=Y^3$ and $Y^2=Y^4$.

Preferably one, two, three or four, very preferably two or four of $Y^1$, $Y^2$, $Y^3$ and $Y^4$ denote M-$R^3$. Particularly preferred are compounds wherein all of $Y^1$ to $Y^4$ denote M-$R^2$, and compounds wherein $Y^1$ and $Y^3$ denote M-$R^2$, and $Y^2$ and $Y^4$ denote A.

In formula I $X^1$ and $X^2$ preferably form together a bivalent group selected from —$CH_2$—, —$CHR^1$— and —$CR^1R^2$—. Therein, $R^1$ and $R^2$ are preferably alkyl with 1 to 8 C atoms, in particular methyl, ethyl or propyl.

Further preferred are compounds wherein $X^1$ and $X^2$ form a bivalent group —$CHR^1$— and $R^1$ is M-$R^3$. Further preferred are compounds wherein $X^1$ and $X^2$ form a bivalent group —$CR^1R^2$— and one or both of, in particular one of $R^1$ and $R^2$ is M-$R^3$.

Further preferred are compounds wherein $X^1$ and $X^2$ together form a 1,1-cycloalkyliden group, in particular 1,1-cyclopentyliden or 1,1-cyclohexyliden.

$X^3$ and $X^4$ are preferably H.

$R^3$ in formula I is preferably different from H.

The cyclic group A is preferably phenyl in which, in addition, one or more CH groups may be replaced by N or cyclohexyl in which, in addition, one or two non-adjacent $CH_2$ groups may be replaced by O and/or S, 1,3-dioxolane-2-yl, cyclohexenylene, bicyclo-(2,2,2)-octylene, piperidine, naphthalene, decahydronaphthalene or 1,2,3,4-tetrahydronaphthalene, it being possible for all these groups to be unsubstituted, mono- or polysubstituted with halogen, cyano or nitro groups or alkyl, alkoxy, alkylcarbonyl or alkoxycarbonyl groups with 1 to 7 C atoms, wherein one or more H atoms may be substituted by F or Cl. Especially preferably A is phenyl or cyclohexyl.

The mesogenic group M is preferably selected of formula II $$-A^1-(Z-A^2)_m-\qquad\qquad II$$

wherein $A^1$ and $A^2$ are independently from one another 1,3- or 1,4-phenylene in which, in addition, one or more CH groups may be replaced by N, 1,3- or 1,4-cyclohexylene in which, in addition, one or two non-adjacent $CH_2$ groups may be replaced by O and/or S, 1,3-dioxolane-4,5-diyl, 1,4-cyclohexenylene, 1,4-bicyclo-(2,2,2)-octylene, piperidine-1,4-diyl, naphthalene-1,6- or -2,6- or -3,6-diyl, decahydronaphthalene-1,6- or -2,6- or -3,6-diyl, 1,2,3,4-tetrahydronaphthalene-1,6- or -2,6- or -3,6-diyl or indane-2,5-diyl, it being possible for all these groups to be unsubstituted, mono- or polysubstituted with halogen, cyano or nitro groups or alkyl, alkoxy, alkylcarbonyl or alkoxycarbonyl groups with 1 to 7 C atoms, wherein one or more H atoms may be substituted by F or Cl, Z is in each case independently —O—, —S—, —CO—, —COO—, —OCO—, —O—COO—, —CO—N($R^0$)—, —N($R^0$)—CO—, —$OCH_2$—, —$CH_2O$—, —$SCH_2$—, —$CH_2S$—, —$CF_2O$—, —$OCF_2$—, —$CF_2S$—, —$SCF_2$—, —$CH_2CH_2$—, —$CF_2CH_2$—, —$CH_2CF_2$—, —$CF_2CF_2$—, —CH=CH—, —CF=CH—, —CH=CF—, —CF=CF—, —C≡C—, —CH=CH—COO—, —OCO—CH=CH— or a single bond, $R^0$ is H or alkyl with 1 to 4 C atoms, and m is 1, 2, 3 or 4.

Very preferred are compounds wherein M incorporates one, two or three, especially two five- or six-membered rings.

Further preferred are compounds wherein at least one of Z is —$CF_2O$—, —$OCF_2$—, —CF=CF—, —CH=CF—, —CF=CH—, —$CH_2CF_2$—, —$CF_2CH_2$— or —$CF_2CF_2$—.

Another preferred embodiment relates to compounds wherein at least one of Z is —C≡C—. These compounds are especially suitable for uses where highly birefringent materials are needed.

Particularly preferred compounds of formula I are those with a mesogenic group M of formula II, wherein m is 1, 2 or 3 and $A^1$ and $A^2$ are selected of 1,4-phenylene and trans-1,4-cyclohexylene, these rings being unsubstituted or substituted in 1 to 4 positions with F, Cl, CN or alkyl, alkoxy, alkylcarbonyl or alkoxycarbonyl with 1 to 4 C-atoms. From these preferred compounds, especially preferred are those comprising a bicyclohexyl or cyclohexylphenyl group.

A smaller group of preferred mesogenic groups M is listed below. For reasons of simplicity, Phe in these groups is 1,4-phenylene which may also substituted by at least one group L, with L being F, Cl, CN or an optionally fluorinated alkyl, alkoxy, alkylcarbonyl or alkoxycarbonyl group with 1 to 4 C atoms, Cyc is 1,4-cyclohexylene and Z has in each case independently one of the meanings of $Z^1$ in formula I. The list of preferred mesogenic groups is comprising the following formulae as well as their mirror images

| | |
|---|---|
| -Phe-Z-Phe- | II-1 |
| -Phe-Z-Cyc- | II-2 |
| -Cyc-Z-Cyc- | II-3 |
| -Phe-Z-Phe-Z-Phe- | II-4 |
| -Phe-Z-Phe-Z-Cyc- | II-5 |
| -Phe-Z-Cyc-Z-Phe- | II-6 |
| -Cyc-Z-Phe-Z-Cyc- | II-7 |
| -Cyc-Z-Cyc-Z-Phe- | II-8 |
| -Cyc-Z-Cyc-Z-Cyc- | II-9 |

Particularly preferred are the subformulae II-1, II-2 and II-3.

The other groups Z are preferably —CF$_2$O—, —OCF$_2$—, —CF$_2$CF$_2$—, —COO—, —OCO—, —CH$_2$CH$_2$— or a single bond.

Another preferred embodiment of the present invention relates to compounds of formula I, wherein $X^1$ and $X^2$ form a bivalent group —CHR$^1$— or —CR$^1$R$^2$— and one or both of, in particular one of $R^1$ and $R^2$ is M-$R^3$, and wherein one or more, preferably all of $Y^1$, $Y^2$, $Y^3$ and $Y^4$ denote M*-$R^3$, with M* being a mesogenic group that contains a structure unit, like for example a 1,3-phenylene group, that is linked non-linearly, at an angle of typically about 120°, to its neighboured groups, thus imparting a bent or banana-shaped structure to the molecule.

In these compounds, M* is preferably -A$^1$-(Z-A$^2$)$_m$-, and the non-linear structure unit is preferably the group $A^1$, which is adjacent to the chiral centre of the compound. Especially preferred non-linear structure units are substituted or unsubstituted 1,3-phenylene, 1,3-cyclohexylene and naphthalene-1,6- or -3,6-diyl.

M* is particularly preferably selected from the groups listed below. Therein Phe* is 1,3-phenylene which may also substituted by at least one group L, with L being F, Cl, CN or an optionally fluorinated alkyl, alkoxy, alkylcarbonyl or alkoxycarbonyl group with 1 to 4 C atoms, and Z, Phe and Cyc have the meanings given above.

| | |
|---|---|
| -Phe*-Z-Phe- | II-10 |
| -Phe*-Z-Cyc- | II-11 |
| -Phe*-Z-Phe-Z-Phe- | II-12 |
| -Phe*-Z-Phe-Z-Cyc- | II-13 |
| -Phe*-Z-Cyc-Z-Phe- | II-14 |

Particularly preferred are the subformulae II-10 and II-11.

Bi- and tricyclic mesogenic groups M and M* are generally preferred. Further preferred are compounds wherein the mesogenic group comprises at least one group Phe that is substituted with one or two groups L, preferably in 3- and/or 5-position, and L is F, Cl, CH$_3$, OCH$_3$, CF$_3$, CHF$_2$, CH$_2$F, OCF$_3$ OCHF$_2$, OCH$_2$F or CN.

L is preferably F, Cl, CN, NO$_2$, CH$_3$, C$_2$H$_5$, OCH$_3$, OC$_2$H$_5$, COCH$_3$, COC$_2$H$_5$, CF$_3$, CHF$_2$, CH$_2$F, OCF$_3$ OCHF$_2$, OCH$_2$F, OC$_2$F$_5$, in particular F, Cl, CN, CH$_3$, C$_2$H$_5$, OCH$_3$, CF$_3$ and OCF$_3$, most preferably F, CH$_3$, CF$_3$, OCH$_3$ and OCF$_3$.

If $R^1$, $R^2$ or $R^3$ in formula I is an alkyl or alkoxy radical, i.e. where the terminal CH$_2$ group is replaced by —O—, this may be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Oxaalkyl, i.e. where one CH$_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

Halogen is preferably F or Cl.

$R^1$, $R^2$ or $R^3$ in formula I can be a polar or an unpolar group. In case of a polar group, it is selected from CN, SF$_5$, halogen, OCH$_3$, SCN, COR$^5$, COOR$^5$ or a mono- oligo- or polyfluorinated alkyl or alkoxy group with 1 to 4 C atoms. $R^5$ is optionally fluorinated alkyl with 1 to 4, preferably 1 to 3 C atoms. Especially preferred polar groups are selected of F, Cl, ON, OCH$_3$, COCH$_3$, COC$_2$H$_5$, COOCH$_3$, COOC$_2$H$_5$, CF$_3$, CHF$_2$, CH$_2$F, OCF$_3$, OCHF$_2$, OCH$_2$F, C$_2$F$_5$ and OC$_2$F$_5$, in particular F, Cl, CN, CF$_3$, OCHF$_2$ and OCF$_3$. In case of an unpolar group, it is preferably alkyl with up to 15 C atoms or alkoxy with 2 to 15 C atoms.

$R^1$, $R^2$ or $R^3$ in formula I can be an achiral or a chiral group. In case of a chiral group it is preferably selected according to formula III:

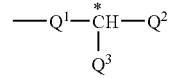

wherein $Q^1$ is an alkylene or alkylene-oxy group with 1 to 9 C atoms or a single bond, $Q^2$ is an alkyl or alkoxy group with 1 to 10 C atoms which may be unsubstituted, mono- or polysubstituted by F, Cl, Br or CN, it being also possible for one or more non-adjacent CH$_2$ groups to be replaced, in each case independently from one another, by —C≡C—, —O—, —S—, —NH—, —N(CH$_3$)—, —CO—, —COO—, —OCO—, —OCO—O—, —S—CO— or —CO—S— in such a manner that oxygen atoms are not linked directly to one another, $Q^3$ is F, Cl, Br, CN or an alkyl or alkoxy group as defined for $Q^2$ but being different from $Q^2$.

In case $Q^1$ in formula III is an alkylene-oxy group, the O atom is preferably adjacent to the chiral C atom.

Preferred chiral groups of formula III are 2-alkyl, 2-alkoxy, 2-methylalkyl, 2-methylalkoxy, 2-fluoroalkyl, 2-fluoroalkoxy, 2-(2-ethin)-alkyl, 2-(2-ethin)-alkoxy, 1,1,1-trifluoro-2-alkyl and 1,1,1-trifluoro-2-alkoxy.

Particularly preferred chiral groups are 2-butyl (=1-methylpropyl), 2-methylbutyl, 2-methylpentyl, 3-methylpentyl, 2-ethylhexyl, 2-propylpentyl, in particular 2-methylbutyl, 2-methylbutoxy, 2-methylpentoxy, 3-methylpentoxy, 2-ethylhexoxy, 1-methylhexoxy, 2-octyloxy, 2-oxa-3-methylbutyl, 3-oxa-4-methylpentyl, 4-methylhexyl, 2-hexyl, 2-octyl, 2-nonyl, 2-decyl, 2-dodecyl, 6-methoxyoctoxy, 6-methyloctoxy, 6-methyloctanoyloxy, 5-methylheptyloxycarbonyl, 2-methylbutyryloxy, 3-methylvaleroyloxy, 4-methylhexanoyloxy, 2-chlorpropionyloxy, 2-chloro-3-methylbutyryloxy, 2-chloro-4-methylvaleryloxy, 2-chloro-3-methylvaleryloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy for example. Very preferred are 2-hexyl, 2-octyl, 2-octyloxy, 1,1,1-trifluoro-2-hexyl, 1,1,1-trifluoro-2-octyl and 1,1,1-trifluoro-2-octyloxy.

In addition, compounds of formula I containing an achiral branched group $R^1$, $R^2$ or $R^3$ may occasionally be of importance, for example, due to a reduction in the tendency towards crystallization. Branched groups of this type generally do not contain more than one chain branch. Preferred achiral branched groups are isopropyl, isobutyl (=methylpropyl), isopentyl (=3-methylbutyl), isopropoxy, 2-methylpropoxy and 3-methylbutoxy.

In another preferred embodiment $R^1$, $R^2$ or $R^3$ in formula I denotes a polymerizable group P-Sp-, with
P being $CH_2=CW-COO-$, $WCH=CH-O-$,

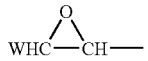

or $CH_2=CH$-Phenyl-$(O)_k-$, W being H, $CH_3$ or Cl and k being 0 or 1, and
Sp being a spacer group having 1 to 25 C atoms or a single bond.

P is preferably a vinyl group, an acrylate group, a methacrylate group, a propenyl ether group or an epoxy group, especially preferably an acrylate or a methacrylate group.

As for the spacer group Sp all groups can be used that are known for this purpose to the skilled in the art. The spacer group Sp is preferably a linear or branched alkylene group having 1 to 20 C atoms, in particular 1 to 12 C atoms, in which, in addition, one or more non-adjacent $CH_2$ groups may be replaced by $-O-$, $-S-$, $-NH-$, $-N(CH_3)-$, $-CO-$, $-O-CO-$, $-S-CO-$, $-O-COO-$, $-CO-S-$, $-CO-O-$, $-CH(halogen)-$, $-CH(CN)-$, $-CH=CH-$ or $-C\equiv C-$.

Typical spacer groups are for example $-(CH_2)_p-$, $-(CH_2CH_2O)_r-CH_2CH_2-$, $-CH_2CH_2-S-CH_2CH_2-$ or $-CH_2CH_2-NH-CH_2CH_2-$, with p being an integer from 2 to 12 and r being an integer from 1 to 3.

Preferred spacer groups are ethylene, propylene, butylene, pentylene, hexylene, heptylene, octylene, nonylene, decylene, undecylene, dodecylene, octadecylene, ethyleneoxyethylene, methyleneoxybutylene, ethylene-thioethylene, ethylene-N-methyl-iminoethylene, 1-methylalkylene, ethenylene, propenylene and butenylene for example.

Especially preferred are inventive chiral compounds of formula I wherein Sp is denoting an alkyl or alkoxy group with 2 to 6 C atoms. Straight-chain alkyl or alkoxy groups are especially preferred.

Particularly preferred compounds of formula I are the following

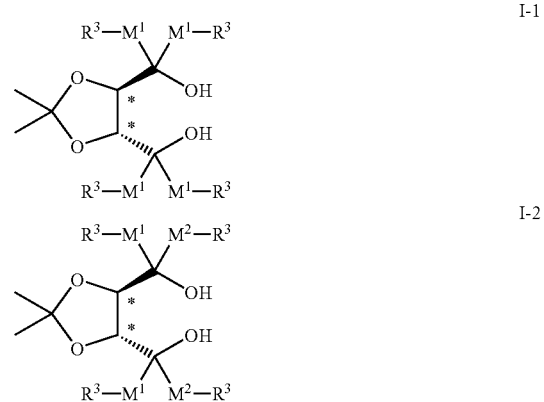

wherein $R^3$ is as defined above and $M^1$ and $M^2$ are different mesogenic groups having one of the meanings of M given above.

Very preferred compounds are those wherein $M^1$-$R^3$ and $M^2$-$R^3$ are selected from the following groups

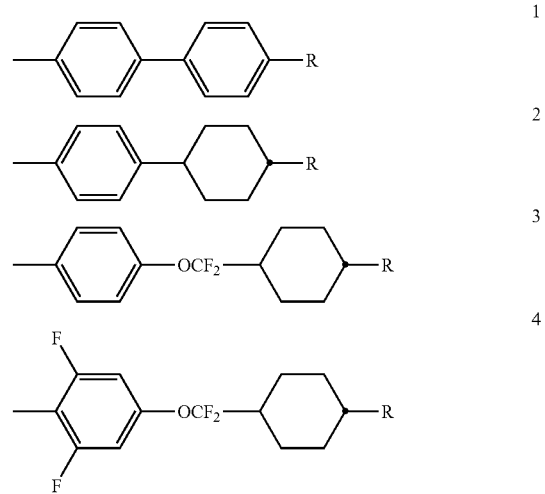

wherein R has one of the meanings of $R^3$ in formula I or of the preferred meanings above, and the 1,4-phenylene rings may also be mono- or polysubstituted by L as described above.

The inventive chiral compounds can be synthesized according to or in analogy to the following reaction schemes.

Scheme 1

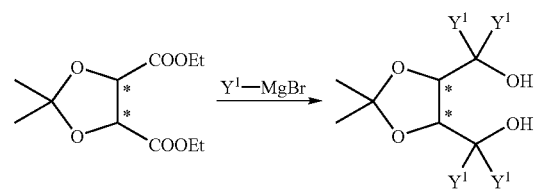

Scheme 2

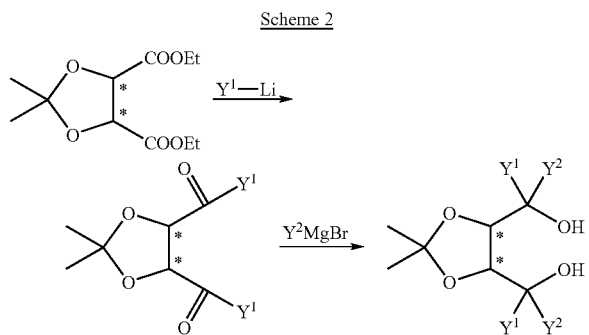

wherein $Y^1$ and $Y^2$ have one of the meanings of formula I.

Further methods of preparing the inventive compounds can be taken from the examples.

The inventive chiral compounds can be used in a liquid crystal mixture for displays exhibiting a twisted molecular structure of the liquid crystal matrix like, for example, supertwisted or active matrix liquid crystal displays, or in displays comprising a liquid crystal mixture with a chiral liquid crystalline phase, like for example chiral smectic or chiral nematic (cholesteric) mixtures for ferroelectric displays or cholesteric displays.

Thus, another object of the invention is a liquid crystalline mixture, in particular a cholesteric liquid crystalline mixture, comprising at least one chiral compound of formula I.

Yet another object of the invention are cholesteric liquid crystal displays comprising a cholesteric liquid crystalline medium containing at least one chiral compound of formula I.

The inventive compounds are especially characterized by a high solubility in liquid crystalline host mixtures. Therefore, they can be added as dopants to liquid crystalline hosts in high amounts without significant affecting the phase behaviour and electrooptical properties of the mixture. Furthermore, undesired spontaneous crystallization at low temperatures are reduced and the operating temperature range of the mixture can be broadened.

Also, even inventive chiral compounds with low values of the HTP can be used for the preparation of highly twisted liquid crystal media, because the dopant concentration can be increased to yield low pitch values (i.e. high twist) without affecting the mixture properties. The use of a second dopant, which is often added to avoid crystallization, can thus be avoided.

In addition, many of the inventive chiral compounds of formula I exhibit high values of the HTP. Thus liquid crystalline mixtures with a high helical twist, i.e. a low pitch, can be prepared by using the inventive compounds, or otherwise a liquid crystalline mixture with a moderate helical twist can be achieved already when using the inventive compounds as dopants in low amounts.

The high HTP values of the inventive compounds makes them also suitable to be used in combination with other compounds for the temperature compensation of the properties of liquid crystal mixtures, such as the cholesteric pitch, and of the properties of displays, e.g. such as the threshold voltage.

As mentioned above, the inventive compounds are furthermore advantageous because they are affecting the physical properties of the liquid crystalline mixture only to a minor extent.

Thus, when admixing the chiral compounds of formula I for example to a liquid crystalline mixture with positive dielectric anisotropy that is used in a liquid crystal display, $\Delta\in$ is being only slightly reduced and the viscosity of the liquid crystalline mixture is increased only to a small extent. This leads to lower voltages and improved switching times of the display when compared to a display comprising conventional dopants.

A liquid crystalline mixture according to the invention comprises preferably 0.1 to 30%, in particular 1 to 25% and very particularly preferably 2 to 15% by weight of chiral compounds of formula I.

A liquid crystalline mixture according to the invention preferably comprises 1 to 3 chiral compounds of formula I.

For temperature compensation applications as described above the liquid crystalline mixture preferably contains a chiral component which contains at least one chiral compound of formula I, and a nematic component comprising one or more nematic or nematogenic compounds.

In a preferred embodiment of the invention the liquid crystalline mixture consist of 2 to 25, preferably 3 to 15 compounds, at least one of which is a chiral compound of formula I. The other compounds, forming the nematic component, are preferably low molecular weight liquid crystalline compounds selected from nematic or nematogenic substances, for example from the known classes of the azoxybenzenes, benzylidene-anilines, biphenyls, terphenyls, phenyl or cyclohexyl benzoates, phenyl or cyclohexyl esters of cyclohehexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexylpyridazines, phenyl- or cyclohexyl-dioxanes, phenyl- or cyclohexyl-1,3-dithianes, 1,2-diphenyl-ethanes, 1,2-dicyclohexylethanes, 1-phenyl-2-cyclohexylethanes, 1-cyclohexyl-2-(4-phenylcyclohexyl)-ethanes, 1-cyclohexyl-2-biphenyl-ethanes, 1-phenyl2-cyclohexylphenylethanes, optionally halogenated stilbenes, benzyl phenyl ether, tolanes, substituted cinnamic acids and further classes of nematic or nematogenic substances. The 1,4-phenylene groups in these compounds may also be laterally mono- or difluorinated.

The liquid crystalline mixture of this preferred embodiment is based on the achiral compounds of this type.

The most important compounds that are posssible as components of these liquid crystalline mixtures can be characterized by the following formula

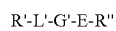

wherein L' and E, which may be identical or different, are in each case, independently from one another, a bivalent radical from the group formed by -Phe-, -Cyc-, -Phe-Phe-, -Phe-Cyc-, -Cyc-Cyc-, -Pyr-, -Dio-, -B-Phe- and -B-Cyc- and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl abd B is 2-(trans-1,4-cyclohexyl)ethyl, pyrimidine-2,5-diyl, pyridine-2,5-diyl or 1,3-dioxane-2,5-diyl.

G' in these compounds is selected from the following bivalent groups —CH=CH—, —N(O)N—, —CH=CY—, —CH=N(O)—, —C≡C—, —CH$_2$—CH$_2$—, —CO—O—, —CH$_2$—O—, —CO—S—, —CH$_2$—S—, —CH=N—, —COO-Phe-COO— or a single bond, with Y being halogen, preferably chlorine, or —CN.

R' and R" are, in each case, independently of one another, alkyl, alkenyl, alkoxy, alkenyloxy, alkanoyloxy, alkoxycarbonyl or alkoxycarbonyloxy with 1 to 18, preferably 3 to 12 C atoms, or alternatively one of R' and R" is F, CF$_3$, OCF$_3$, Cl, NCS or CN.

In most of these compounds R' and R" are, in each case, independently of each another, alkyl, alkenyl or alkoxy with different chain length, wherein the sum of C atoms in nematic media generally is between 2 and 9, preferably between 2 and 7.

Many of these compounds or mixtures thereof are commercially available. All of these compounds are either known or can be prepared by methods which are known per se, as described in the literature (for example in the standard works such as Houben-Weyl, Methoden der Organischen Chemie [Methods of Organic Chemistry], Georg-Thieme-Verlag, Stuttgart), to be precise under reaction conditions which are known and suitable for said reactions. Use may also be made here of variants which are known per se, but are not mentioned here.

The inventive compounds are in particular useful for anisotropic polymer gels and for low molar mass or polymerizable or polymerized cholesteric liquid crystalline mixtures for cholesteric displays, such as for example phase change displays or surface stabilized or polymer stabilized cholesteric texture displays (SSCT, PSCT).

A particularly preferred embodiment of the invention relates to chiral compounds showing a low temperature dependence of the HTP in nematic liquid crystal mixtures. These compounds are useful for cholesteric liquid crystalline mixtures and displays with a low temperature dependence of the reflection wavelength dλ/dT (T=temperature, λ=reflection wavelength maximum).

In particular, it was found that when using chiral compounds of formula I in cholesteric liquid crystalline media, for example for application in an SSCT or PSCT display, they exhibit good solubility in the nematic host mixture and induce a high helical twist with low temperature dependence of the helical pitch and the reflection wavelength. Thus, cholesteric mixtures with high brightness of the reflection colour and low temperature dependence can be achieved even by using only one chiral dopant according to formula I, preferably in low amounts. This is a considerable advantage over prior art, where high amounts of dopants are needed, and where it is often necessary to use two or more dopants with opposite temperature dependence of the helical twist (e.g. one with positive temperature dependence and one with negative temperature dependence) to achieve good temperature compensation of the reflection wavelength.

Thus, a particularly preferred embodiment of the present invention relates to a cholesteric liquid crystalline medium, in particular for use in SSCT and PSCT displays, comprising one chiral compound of formula I, preferably in an amount of 15% or less, in particular 10% or less, very preferably 5% or less.

Another preferred embodiment relates to inventive chiral compounds with a strong temperature dependence of the HTP in nematic liquid crystal mixtures, which are useful for thermochromic media.

Cholesteric displays are described for example in WO 92/19695, WO 93/23496, U.S. Pat. Nos. 5,453,863 or 5,493,430, with the entire disclosure of these documents being introduced into this application by way of reference.

Furthermore, anisotropic polymer gels and displays comprising them are disclosed for example in DE 195 04 224 and GB 2 279 659.

It has been found that SSCT and PSCT displays comprising the inventive compounds have reduced response times, lower voltages and improved contrast compared to displays comprising conventional dopants, like e.g. R 811 or CB 15, that are commercially available by Merck KGaA (Darmstadt, Germany). For example, SSCT and PSCT displays in which the conventional dopants are replaced by chiral compounds of according to the present invention can show reduced switching time.

Cholesteric films made by using the inventive compounds instead of prior art dopants show improved brightness, leading to a better contrast between the coloured planar texture and the almost clear focal conic state which is made black using a black backplate.

The inventive chiral compounds and polymerizable liquid crystalline mixtures comprising these compounds are also particularly useful for the preparation of anisotropic polymer films with a chiral liquid crystalline phase, such as cholesteric or chiral smectic polymer films, in particular films that exhibit helically twisted molecular structure with uniform planar orientation, i.e. wherein the helical axis is oriented perpendicular to the plane of the film.

For example, oriented cholesteric polymer films can be used as broad waveband reflective polarizers, as described e.g. in EP 0 606 940, as colour filters, for security markings, or for the preparation of liquid crystal pigments. I. Heyndericks and D. J. Broer in Mol. Cryst. Liq. Cryst. 203, 113–126 (1991) describe crosslinked cholesteric polymer films that are made of liquid crystalline diacrylates and contain a low molecular weight chiral dopant.

It has been found that cholesteric polymer films made by using the inventive chiral compounds are brighter compared to films comprising dopants of prior art like e.g. R 811 or CB 15 as mentioned above.

For the preparation of anisotropic polymer gels or oriented polymer films, the liquid crystalline mixture should comprise at least one polymerizable compound, preferably a polymerizable mesogenic compound, in additon to chiral compounds of formula I.

Thus, another object of the invention are polymerizable liquid crystalline mixtures comprising at least one chiral compound of formula I and at least one polymerizable mesogenic compound.

Examples of suitable polymerizable mesogenic compounds that can be used as components of the polymerizable CLC material, are disclosed for example in WO 93/22397; EP 0,261,712; DE 195,04,224; WO 95/22586 and WO 97/00600. The compounds disclosed in these documents, however, are to be regarded merely as examples that shall not limit the scope of this invention. Preferably the polymerizable CLC mixture comprises at least one polymerizable mesogenic compound having one polymerizable functional group and at least one polymerizable mesogenic compound having two or more polymerizable functional groups.

Examples of especially useful monoreactive chiral and achiral polymerizable mesogenic compounds are shown in the following list of compounds, which should, however, be taken only as illustrative and is in no way intended to restrict, but instead to explain the present invention:

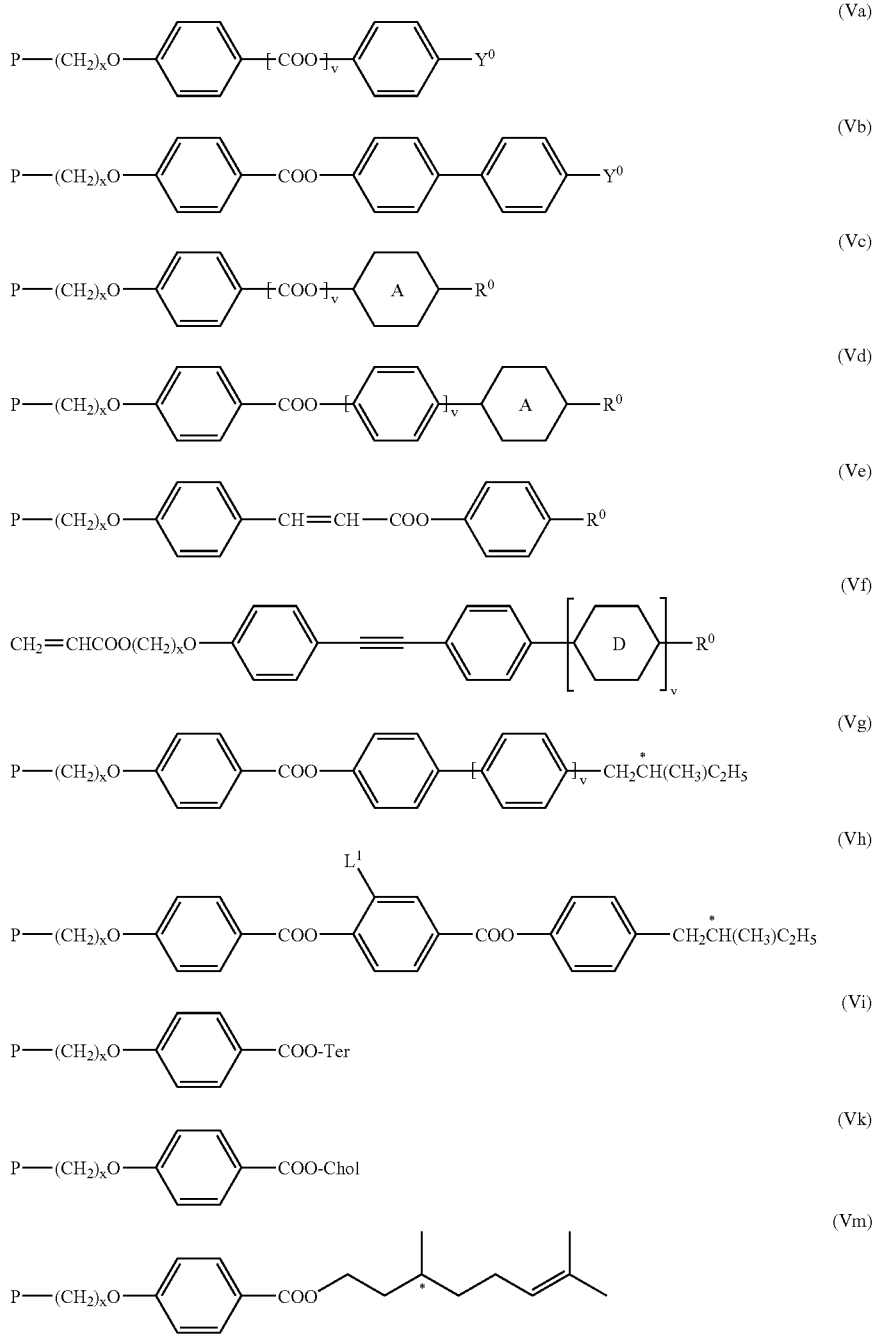

wherein, P has one of the meanings given above, x is an integer from 1 to 12, A and D are 1,4-phenylene or 1,4-cyclohexylene, v is 0 or 1, $Y^0$ is a polar group, $R^0$ is an unpolar alkyl or alkoxy group, Ter is a terpenoid radical like e.g. menthyl, Chol is a cholesteryl group, and $L^1$ and $L^2$ are each independently H, F, Cl, CN, OH, $NO_2$ or an optionally halogenated alkyl, alkoxy or carbonyl group with 1 to 7 C atoms.

The polar group $Y^0$ is preferably CN, $NO_2$, halogen, $OCH_3$, OCN, SCN, $COR^5$, $COR^5$ or a mono- oligo- or polyfluorinated alkyl or alkoxy group with 1 to 4 C atoms. $R^5$ is optionally fluorinated alkyl with 1 to 4, preferably 1 to 3 C atoms. Especially preferably the polar group $Y^0$ is selected of F, Cl, CN, $NO_2$, $OCH_3$, $COCH_3$, $COC_2H_5$, $COOCH_3$, $COOC_2H_5$, $CF_3$, $C_2F_5$, $OCF_3$, $OCHF_2$, and $OC_2F_5$, in particular F, Cl, CN, $OCH_3$ and $OCF_3$.

The unpolar group $R^0$ is preferably an alkyl group with 1 or more, preferably 1 to 15 C atoms or an alkoxy group with 2 or more, preferably 2 to 15 C atoms.

Examples of useful direactive chiral and achiral polymerizable mesogenic compounds are shown in the following list of compounds, which should, however, be taken only as illustrative and is in no way intended to restrict, but instead to explain the present invention

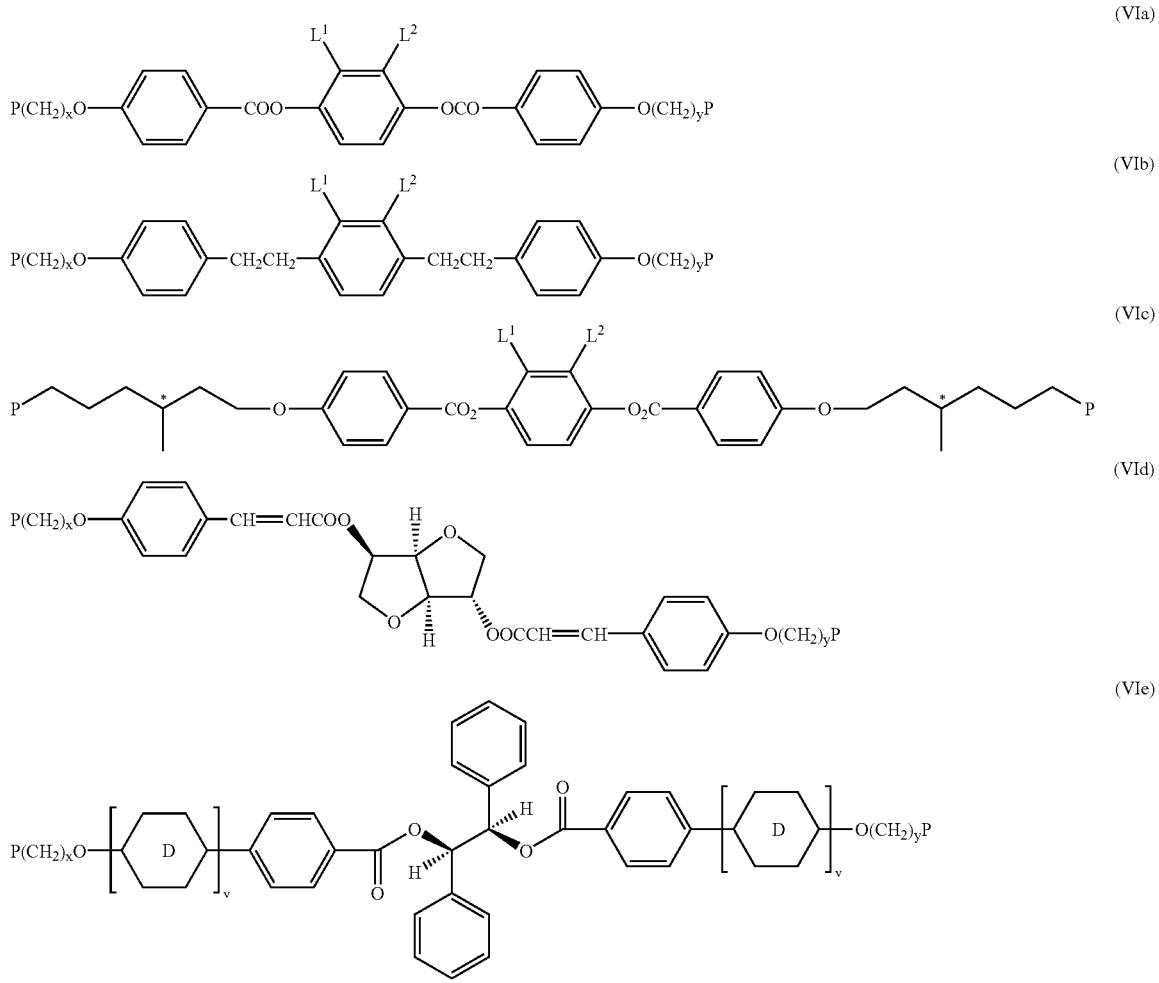

wherein P, x, D, $L^1$ and $L^2$ have one of the meanings given above and y is an integer from 1 to 12 the same as or different from x.

A polymerizable CLC material according to the first preferred embodiment as described above comprises one or more chiral dopants which themselves do not necessarily have to show a liquid crystalline phase and give good planar alignment themselves, in particular non-polymerizable chiral dopants.

The mono- and difunctional polymerizable mesogenic compounds of above formulae V and VI can be prepared by methods which are known per se and which are described in the documents cited above and, for example, in standard works of organic chemistry such as, for example, Houben-Weyl, Methoden der organischen Chemie, Thieme-Verlag, Stuttgart.

In a preferred embodiment of the invention the polymerizable liquid crystalline mixtures comprise at least one inventive chiral compound, at least one monofunctional compound of formulae Va-Vm and at least one bifunctional polymerizable compound of formulae VIa-VIe.

In another preferred embodiment the polymerizable liquid crystalline mixtures comprise at least one inventive chiral compound and at least two monofunctional compounds of formulae Va-Vm.

Another object of the invention is an anisotropic polymer film with an oriented chiral liquid crystalline phase obtainable by (co)polymerizing a liquid crystalline mixture comprising at least one chiral compound of formula I and at least one polymerizable mesogenic compound preferably selected of formula Va-Vm and VIa-VIe and/or at least one polymerizable chiral compound of formula I.

To prepare anisotropic polymer film with a chiral liquid crystalline phase with uniform orientation the inventive liquid crystalline mixtures, for example, are coated onto a substrate, aligned and polymerized in situ by exposing them to heat or actinic radiation. Alignment and curing are preferably carried out in the liquid crystalline phase of the liquid crystalline mixtures.

Actinic radiation means irradiation with light, like UV light, IR light or visible light, irradiation with X-rays or gamma rays or irradiation with high energy particles, such as ions or electrons. As a source for actinic radiation for example a single UV lamp or a set of UV lamps can be used. Another possible source for actinic radiation is a laser, like e.g. a UV laser, an IR laser or a visible laser.

For example, when polymerizing by means of UV light, a photoinitiator can be used that decomposes under UV irradiation to produce free radicals or ions that start the polymerization reaction.

It is also possible to use a cationic photoinitiator, when curing reactive mesogens with for example vinyl and epoxide reactive groups, that photocures with cations instead of free radicals.

As a photoinitiator for radical polymerization for example the commercially available Irgacure 651, Irgacure 184, Darocure 1173 or Darocure 4205 (all from Ciba Geigy AG) can be used, whereas in case of cationic photopolymerization the commercially available UVI 6974 (Union Carbide) can be used.

Preferably the polymerizable liquid crystalline mixtures comprising polymerizable chiral compounds of formula I and/or polymerizable mesogenic compounds of formulae V and VI additionally comprise 0.01 to 10%, in particular 0.05 to 8%, very preferably 0.1 to 5% by weight of a photoinitiator, especially preferably a UV-photoinitiator.

In a preferred embodiment of the invention the polymerization of the polymerizable mesogenic material is carried out under an atmosphere of inert gas, preferably under a nitrogen atmosphere.

As a substrate for example a glass or quarz sheet as well as a plastic film or sheet can be used. It is also possible to put a second substrate on top of the coated mixture prior to, during and/or after polymerization. The substrates can be removed after polymerization or not. When using two substrates in case of curing by actinic radiation, at least one substrate has to be transmissive for the actinic radiation used for the polymerization.

Isotropic or birefringent substrates can be used. In case the substrate is not removed from the polymerized film after polymerization, preferably isotropic substrates are used.

Preferably at least one substrate is a plastic substrate such as for example a film of polyester such as polyethyleneterephthalate (PET), of polyvinylalcohol (PVA), polycarbonate (PC) or triacetylcellulose (TAC), especially preferably a PET film or a TAC film. As a birefringent substrate for example an uniaxially stretched plastic film can be used. For example PET films are commercially available from ICI Corp. under the trade name Melinex.

In a preferred embodiment of the present invention, the inventive mixture of the polymerizable liquid crystalline mixture comprising a chiral compound of formula I is coated as a thin layer on a substrate or between substrate, and is preferably aligned in its chiral mesophase, eg. the cholesteric or chiral smectic phase, to give a planar orientation, i.e. an orientation so that the axis of the molecular helix extends transversely to the layer.

A planar orientation can be achieved for example by shearing the mixture, e.g. by means of a doctor blade. It is also possible to apply an alignment layer, for example a layer of rubbed polyimide or sputtered $SiO_x$, on top of at least one of the substrates.

In another preferred embodiment, a second substrate is put on top of the coated material. In this case, the shearing caused by putting together the two substrates is sufficient to give good alignment.

It is also possible to apply an electric or magnetic field to the coated mixture.

In some cases it is of advantage to apply a second substrate not only to aid alignment of the polymerizable mixture but also to exclude oxygen that may inhibit the polymerization. Alternatively the curing can be carried out under an atmosphere of inert gas. However, curing in air is also possible using suitable photoinitiators and high lamp power. When using a cationic photoinitiator oxygen exclusion most often is not needed, but water should be excluded.

A detailed description of the in situ polymerization of polymerizable mesogenic compounds can be found in D. J. Broer et al., Makromolekulare Chemie 190, 2255 (1989).

A polymerizable liquid crystalline mixture for the preparation of anisotropic polymer films comprises preferably 0.1 to 35%, in particular 0.5 to 15% and very particularly preferably 0.5 to 5% by weight of one or more polymerizable chiral compounds of formula I.

Polymerizable liquid crystalline mixtures are preferred that comprise 1 to 3 chiral compounds of formula I.

The inventive polymerizable liquid crystalline mixtures can additionally comprise one or more other suitable components, such as, for example, catalysts, sensitizers, stabilizers, co-reacting monomers or surface-active compounds.

In a preferred embodiment of the invention, the inventive polymerizable liquid crystalline mixture comprises a stabilizer that is used to prevent undesired spontaneous polymerization for example during storage of the composition. As stabilizers in principal all compounds can be used that are known to the skilled in the art for this purpose. These compounds are commercially available in a broad variety. Typical examples for stabilizers are 4-ethoxyphenol or butylated hydroxytoluene (BHT).

It is also possible, in order to increase crosslinking of the polymers, to add up to 20% of a non mesogenic compound with two or more polymerizable functional groups to the polymerizable composition alternatively or additionally to the multifunctional polymerizable mesogenic compounds.

Typical examples for difunctional non mesogenic monomers are alkyldiacrylates or alkyldimethacrylates with alkyl groups of 1 to 20 C atoms. Typical examples for non mesogenic monomers with more than two polymerizable groups are trimethylpropanetrimethacrylate or pentaerythritoltetraacrylate.

Polymerization of inventive compositions comprising compounds with only one polymerizable functional group leads to linear polymers, whereas in the presence of compounds with more than one polymerizable functional group crosslinked polymers are obtained.

For the preparation of anisotropic polymer gels, the liquid crystalline mixtures can be polymerized in situ as described above, however, in this case alignment of the polymerizable mixture is not necessary.

The inventive chiral compounds of formula I can also be used for the prepration of thermochromic liquid crystalline mixtures. Such mixtures are characterized in that they exhibit a chiral liquid crystalline phase or chiral mesophase, like e.g. a chiral smectic phase or a chiral nematic (=cholesteric) phase, with a helically twisted molecular structure that shows selective reflection of a specific waveband of light, wherein the pitch of the molecular helix and thereby the reflected wavelengths are depending on the temperature.

Especially preferred are inventive liquid crystalline mixtures with thermochromic behaviour that exhibit a cholesteric phase. Of these preferred compositions, further preferred are compositions that exhibit a cholesteric phase and a smectic phase, most preferably a chiral smectic phase, at temperatures below the temperature range of the cholesteric phase. The inventive liquid crystalline mixtures exhibiting thermochromic behaviour can be polymerizable or non-polymerizable.

The inventive chiral compounds of formula I and liquid crystalline mixtures, liquid crystal polymers or liquid crystal pigments comprising them are also suitable for use in cosmetic and pharmaceutical compositions, for example for coloured make-up as described in EP 815 826 or as UV-filters for the protection of human skin or hair, in particular protection against UV-A and UV-B-radiation, as described for example in DE 196 29 761 or EP 1 038 941. The inventive dopants have a high HTP, therefore only small amounts are needed to yield a short pitch, resulting in a material that shows reflection in the UV range and is suitable as UV-filter.

A liquid crystalline mixture, liquid crystal polymer or liquid crystal pigment comprising a chiral compound of formula I and reflecting UV light, in particular of a wavelength of 200 to 400 nm, is another object of the invention. Another object is a cosmetic composition, in particular a cosmetic or pharmaceutical composition for protection of human skin or hair, comprising as UV-filter a liquid crystalline mixture, liquid crystal polymer or liquid crystal pigment comprising a chiral compound of formula I and reflecting UV light, in particular in a wavelength range of 200–440 nm, especially 280–400 nm, 200–230 nm (UV-C) and 280–330 nm (UV-B).

From the foregoing description, one skilled in the art can easily ascertain the essential characteristics of this invention, and without departing from the spirit and scope thereof, can make various changes and modifications of the invention to adapt it to various usages and conditions.

Without further elaboration, it is believed that one skilled in the art can, using the preceding description, utilize the present invention to ist fullest extent. The following examples are, therefore, to be construed as merely illustrative and not limitative of the remainder of the disclosure in any way whatsoever.

In the foregoing and in the following examples, unless otherwise indicated, all temperatures are set forth uncorrected in degrees Celsius and all parts and percentages are by weight.

The values of the helical twisting power HTP of a chiral compound in a liquid crystalline host are given according to the equation $HTP=(p*c)^{-1}$ in $\mu m^{-1}$, wherein p is the pitch of the molecular helix, given in $\mu m$, and c is the concentration by weight of the chiral compound in the host given in relative values (thus, e.g. a concentration of 1% by weight is corresponding to a value of c of 0.01).

The following abbreviations are used to illustrate the liquid crystalline phase behaviour of the compounds: K=crystalline; N=nematic; S=smectic; N*, Ch=chiral nematic, cholesteric; I=isotropic. The numbers between these symbols indicate the phase transition temperatures in degree Celsius. Furthermore, $\Delta n$ is the birefringence at 589 nm and 20° C. and $\Delta \in$ is the dielectric anisotropy at 20° C. C* in a chemical formula denotes a chiral C atom.

Unless indicated otherwise, the HTP values of the examples were determined in the commercially available liquid crystal host mixture MLC-6260 (Merck KGaA, Darmstadt, Germany) at a concentration of 1% and a temperature of 20° C.

EXAMPLE 1

Compound (1) was prepared as follows

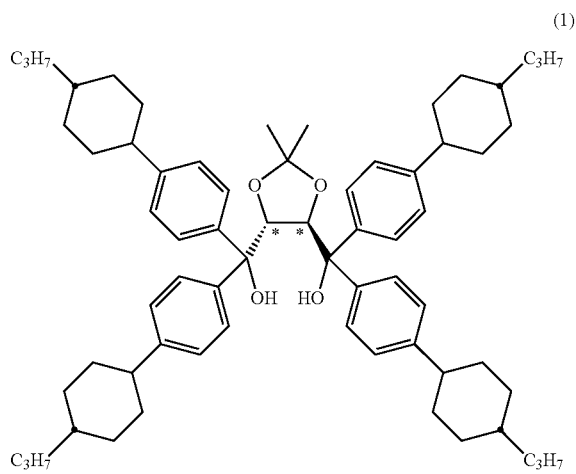

0.943 g (0.0388 mol) Mg were reacted with 10.0 g (0.0355 mol) 4-Bromo-(4'-propylcyclohexyl)-benzene according to Grignard in 50 ml THF. Then 1.411 g (0.0065 mol) 2,2-Dimethyl-[1,3]dioxolane-4,5-dicarboxylic acid dimethyl ester were added under cooling with ice, the mixture stirred for 20 minutes at room temperature and for 2 hours under reflux. The mixture was poured onto a mixture of 100 ml saturated ammonium chloride solution and 50 g ice. The separated aqueous phase was extracted with MTB ether and the combined organic phases washed with saturated sodium chloride solution and dried over $Na_2SO_4$. After evaporation of the solvent the residue was filtered with silica gel in n-hexane and the product eluted with n-hexane/ethyl acetate 20:1. The crude product was purified by flash chromatography in n-hexane/ethyl acetate 30:1.

Compound (1) has a HTP of 11.5 with a low temperature dependence (10.1 at 0° C. and 13.4 at 50° C.).

EXAMPLE 2

Compound (2) was prepared according to the reaction scheme below

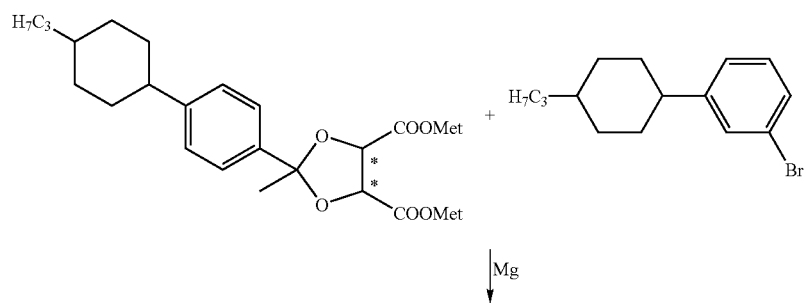

-continued

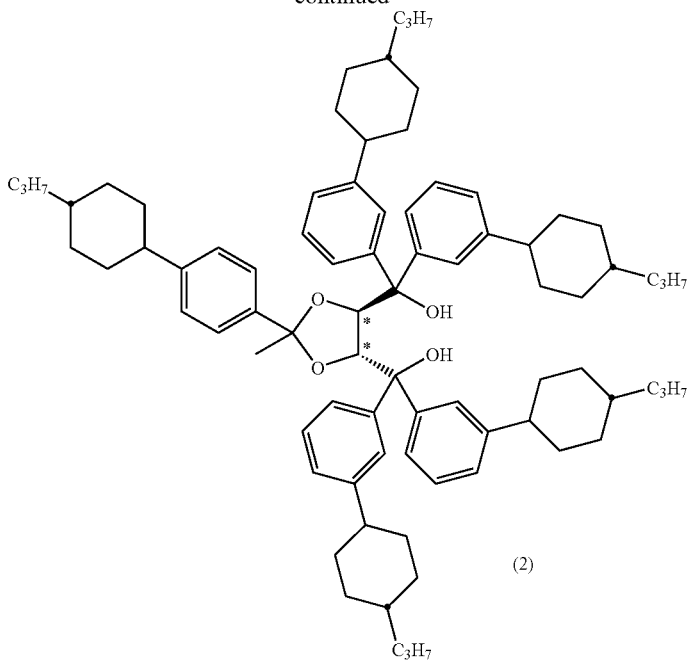

(2)

The reaction was carried out as described in example 1.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various conditions and usages.

What is claimed is:

1. A chiral compound of the formula I

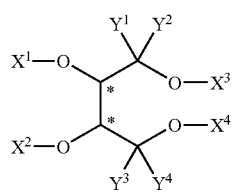

wherein $X^1$ and $X^2$ form together a bivalent radical selected from —CH$_2$—, —CHR$^1$—, —CR$^1$R$^2$—, —SiR$^1$R$^2$— or 1,1-cycloalkyliden, $X^3$ and $X^4$ are H or have one of the meanings given for $X^1$ and $X^2$, $Y^1$, $Y^2$, $Y^3$ and $Y^4$ are each independently as defined for $R^1$, A or -M-R$^3$, A is a cyclic group, M is a mesogenic group, $R^1$ and $R^2$ have independently from each other one of the meanings of $R^3$ or -M-R$^3$, and $R^3$ is:

H, F, Cl, Br, CN, SCN, or SF$_5$, or a chiral or achiral alkyl group with 1 to 30 C atoms which is unsubstituted, or mono- or polysubstituted by F, Cl, Br or CN, one or more non-adjacent CH$_2$ groups optionally being replaced, in each case independently from one another, by —O—, —S—, —NH—, —N(CH$_3$)—, —CO—, —COO—, —OCO—, —OCO—O—, —S—CO—, —CO—S—, —CH=CH— or —C≡C— in such a manner that oxygen atoms are not linked directly to one another, or a polymerizable group, wherein at least one of $Y^1$, $Y^2$, $Y^3$ and $Y^4$ is -M-R$^3$, and wherein at least one group M in the compound is of formula II -A$^1$-(Z-A$^2$)$_m$-    II wherein $A^1$ and $A^2$ are independently from one another 1,3- or 1,4-phenylene in which one or more CH groups are optionally replaced by N; 1,3- or 1,4-cyclohexylene in which one or two non-adjacent CH$_2$ groups are optionally replaced by O and/or S; 1,3-dioxolane-4,5-diyl; 1,4-cyclohexenylene; 1,4-bicyclo-(2,2,2)-octylene; piperidine-1,4-diyl; decahydronaphthalene-1,6- or -2,6- or -3,6-diyl; 1,2,3,4-tetrahydronaphthalene-1, 6- or -2,6- or -3,6-diyl; or indane-2,5-diyl; all these groups being unsubstituted, or mono- or polysubstituted with halogen, cyano or nitro groups or alkyl, alkoxy, alkylcarbonyl or alkoxycarbonyl groups with 1 to 7 C atoms, wherein one or more H atoms are optionally substituted by F or Cl, Z is in each case independently —O—, —S—, —CO—, —COO—, —OCO—, —O—COO—, —CO—N(R$^0$)—, —N(R$^0$)—CO—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=CH—, —CF=CH—, —CH=CF—, —CF=CF—, —C≡C—, —CH=CH—COO—, —OCO—CH=CH— or a single bond, R⁰ is H or alkyl with 1 to 4 C atoms, and m is in each case independently 1, 2, 3 or 4, provided that all of Y¹, Y², Y³ and Y⁴ are not simultaneously -M-R³ wherein A¹ and A² are 1,4-phenylene, Z is a single bond, m is 1 and R³ is H.

2. A chiral compound according to claim 1, wherein X¹ and X² form together a bivalent group selected from —CH₂—, —CHR¹— and —CR¹R²—.

3. A chiral compound according to claim 2, wherein X¹ and X² form a bivalent group —CHR¹— or —CR¹R²— and one or both of R¹ and R² is -M-R³.

4. A chiral compound according to claim 1, wherein X³ and X⁴ are H.

5. A chiral compound according to claim 1, wherein each M is of formula II

-A¹-(Z-A²)$_m$-     II wherein

A¹ and A² are independently from one another 1,3- or 1,4-phenylene in which one or more CH groups are optionally replaced by N; 1,3- or 1,4-cyclohexylene in which one or two non-adjacent CH₂ groups are optionally replaced by O and/or S; 1,3-dioxolane-4,5-diyl; 1,4-cyclohexenylene; 1,4-bicyclo-(2,2,2)-octylene; piperidine-1,4-diyl; decahydronaphthalene-1,6- or -2,6- or -3,6-diyl; 1,2,3,4-tetrahydronaphthalene-1,6- or -2,6- or -3,6-diyl; or indane-2,5-diyl; all these groups being unsubstituted, or mono- or polysubstituted with halogen, cyano or nitro groups or alkyl, alkoxy, alkylcarbonyl or alkoxycarbonyl groups with 1 to 7 C atoms, wherein one or more H atoms are optionally substituted by F or Cl, Z is in each case independently —O—, —S—, —CO—, —COO—, —OCO—, —O—COO—, —CO—N(R⁰)—, —N(R⁰)—CO—, —SCH₂—, —CH₂S—, —CF₂O—, —OCF₂—, —CF₂S—, —SCF₂—, —CH₂CH₂—, —CF₂CH₂—, —CH₂CF₂—, —CF₂CF₂—, —CH=CH—, —CF=CH—, —CH=CF—, —CF=CF—, —C≡C—, —CH=CH—COO—, —OCO—CH=CH— or a single bond, R⁰ is H or alkyl with 1 to 4 C atoms, and m is in each case independently 1, 2, 3 or 4 provided that all of Y¹, Y², Y³ and Y⁴ are not simultaneously -M-R³ wherein A¹ and A² are 1,3- or 1,4-phenylene, Z is a single bond, m is 1 and R³ is H.

6. A chiral compound according to claim 1, wherein M is selected from the following formulae and their mirror images -Phe-Z-Phe-     II-1

-Phe-Z-Cyc-    II-2

-Cyc-Z-Cyc-    II-3

-Phe-Z-Phe-Z-Phe-    II-4

-Phe-Z-Phe-Z-Cyc-    II-5

-Phe-Z-Cyc-Z-Phe-    II-6

-Cyc-Z-Phe-Z-Cyc-    II-7

-Cyc-Z-Cyc-Z-Phe-    II-8

-Cyc-Z-Cyc-Z-Cyc-    II-9 wherein Phe is 1,4-phenylene which is optionally substituted by at least one group L, with L being F, Cl, CN or an optionally fluorinated alkyl, alkoxy, alkylcarbonyl or alkoxycarbonyl group with 1 to 4 C atoms, Cyc is 1,4-cyclohexylene and Z is —CF₂O—, —OCF₂—, —CF₂CF₂—, —COO—, —OCO—, —CH₂CH₂— or a single bond.

7. A chiral compound according to claim 3, wherein one or more of Y¹, Y², Y³ and Y⁴ denote M*-R³, with M* being -A¹-(Z-A²)$_m$-, wherein A¹ is selected from substituted or unsubstituted 1,3-phenylene, or 1,3-cyclohexylene, A² is 1,3- or 1,4-phenylene in which one or more CH groups are optionally replaced by N; 1,3- or 1,4-cyclohexylene in which one or two non-adjacent CH₂ groups are optionally replaced by O and/or S; 1,3-dioxolane-4,5-diyl; 1,4-cyclohexenylene; 1,4-bicyclo-(2,2,2)-octylene; piperidine-1,4-diyl; decahydronaphthalene-1,6- or -2,6- or -3,6-diyl; 1,2,3,4-tetrahydronaphthalene-1,6- or -2,6- or -3,6-diyl; or indane-2,5-diyl; all these groups being unsubstituted, or mono- or polysubstituted with halogen, cyano or nitro groups or alkyl, alkoxy, alkylcarbonyl or alkoxycarbonyl groups with 1 to 7 C atoms, wherein one or more H atoms are optionally substituted by F or Cl, Z is in each case independently —O—, —S—, —CO—, —COO—, —OCO—, —O—COO—, —CO—N(R⁰)—, —N(R⁰)—CO—, —SCH₂—, —CH₂S—, —CF₂O—, —OCF₂—, —CF₂S—, —SCF₂—, —CH₂CH₂—, —CF₂CH₂—, —CH₂CF₂—, —CF₂CF₂—, —CH=CH—, —CF=CH—, —CH=CF—, —CF=CF—, —C≡C—, —CH=CH—COO—, —OCO—CH=CH— or a single bond, and m is in each case independently 1, 2, 3 or 4.

8. A chiral compound according to claim 1, wherein at least one of the groups R¹, R² or R³ is a polymerizable group P-Sp-, with P being CH₂=CW—COO—, WCH=CH—O—,

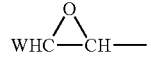

or CH₂=CH-Phenyl-(O)$_k$—, W being H, CH₃ or Cl and k being 0 or 1, and

Sp being a spacer group having 1 to 25 C atoms or a single bond.

9. A liquid crystalline mixture comprising at least one chiral compound according to claim 1.

10. A cholesteric liquid crystalline medium comprising a chiral component which contains one or more chiral compounds according to claim 1, and a nematic component which contains one or more nematic or nematogenic compounds.

11. An SSCT display comprising a medium according to claim 10.

12. A chiral linear or crosslinked liquid crystalline polymer obtained by polymerizing a compound according to claim 8.

13. A chiral linear or crosslinked liquid crystalline polymer obtained by polymerizing a compound according to claim 1, wherein at least one group in the compound is a polymerizable group.

14. A liquid crystal display comprising a compound according to claim 1.

15. A liquid crystal display comprising a liquid crystalline mixture of claim 9.

16. A liquid crystal display according to claim 18, which is an STN, TN, AMD-TN, temperature compensation, ferroelectric, guest-host, phase change or surface stabilized or polymer stabilized cholesteric texture display.

17. An active or passive optical element comprising a liquid crystalline mixture according to claim 9.

18. An active or passive optical element according to claim 17, which is a polarizer, compensator, alignment layer, color filter or holographic element.

19. An adhesive, synthetic resin with anisotropic mechanical properties, cosmetic or pharmaceutical composition comprising a liquid crystalline mixture according to claim 9.

20. A composition of claim 19, which is a UV filter, a diagnostic agent, a chiral dopant or a liquid crystal pigment, or is used in connection with: a decorative or security application, nonlinear optics, or optical information storage.

21. A chiral compound according to claim 1, wherein the cyclic group A is: phenyl in which one or more CH groups are optionally replaced by N; cyclohexyl in which one or two non-adjacent $CH_2$ groups are optionally replaced by O and/or S; 1,3-dioxolane-2-yl, cyclohexenylene; bicyclo-(2,2,2)-octylene; piperidine; naphthalene; decahydronaphthalene; or 1,2,3,4-tetrahydronaphthalene; wherein all of these groups are unsubstituted, or mono- or polysubstituted with halogen, cyano or nitro groups or alkyl, alkoxy, alkylcarbonyl or alkoxycarbonyl groups with 1 to 7 C atoms, wherein one or more H atoms are optionally substituted by F or Cl.

* * * * *

UNITED STATES PATENT AND TRADEMARK OFFICE
CERTIFICATE OF CORRECTION

PATENT NO. : 7,041,345 B2
APPLICATION NO. : 10/332807
DATED : May 9, 2006
INVENTOR(S) : Peer Kirsch Page 1 of 1

It is certified that error appears in the above-identified patent and that said Letters Patent is hereby corrected as shown below:

Column 24, line 66, reads "one group" should read -- one $R^3$ group --
Column 25, line 5, reads "according to claim 18," should read -- according to claim 15, --

Signed and Sealed this

Twenty-seventh Day of May, 2008

JON W. DUDAS
*Director of the United States Patent and Trademark Office*